United States Patent [19]

Gassen et al.

[11] Patent Number: 5,087,775
[45] Date of Patent: Feb. 11, 1992

[54] PROCESS FOR THE PREPARATION OF PARTIALLY FLUORINATED ALCOHOLS

[75] Inventors: Karl-Rudolf Gassen, Odenthal; Dietmar Bielefeldt, Ratingen; Michael Negele, Cologne; Heinz Ziemann, Leichlingen, all of Fed. Rep. of Germany

[73] Assignee: Bayer Aktiengesellschaft, Leverkusen, Fed. Rep. of Germany

[21] Appl. No.: 604,026

[22] Filed: Oct. 24, 1990

[30] Foreign Application Priority Data

Nov. 30, 1989 [DE] Fed. Rep. of Germany ....... 3939535

[51] Int. Cl.$^5$ .............................................. C07C 31/34
[52] U.S. Cl. .................................... 568/842; 568/667; 568/669; 568/671; 568/683; 568/685; 568/838; 568/839; 568/865; 568/866
[58] Field of Search ............... 568/842, 839, 838, 669, 568/683, 865, 866, 667, 685, 671

[56] References Cited

PUBLICATIONS

72 *JACS*, "Reactions of Polyfluoro Olefins", Barr et al, 1950, pp. 4480–4482.
"Methyl Vinyl Ether", General Aniline and Film Corp., 1973, p. 6.
*Organic Chemistry*, 3rd Edition, Morrison et al, 1973, pp. 505–506.
*Organic Chemistry*, 4th Edition, Morrison et al, 1983, pp. 539–540.
JACS, 85, 1963, p. 1613, left col., "Hydrogenlysis of VJ Formation of Bibenzyl".
Chemistry of Organic Fluorine Compounds, p. 271, Equation 736.
Journal of General Chemistry of the USSR, vol. 34, No. 7, Jul. 1964.

Primary Examiner—Howard T. Mars
Assistant Examiner—R. Cook
Attorney, Agent, or Firm—Sprung Horn Kramer & Woods

[57] ABSTRACT

A process for the preparation of partially fluorinated alcohols starting from halogen-containing alkenes, and 2,2,3,3,4,4-hexafluorocyclopentanol as a new partially fluorinated alcohol.

8 Claims, No Drawings

PROCESS FOR THE PREPARATION OF PARTIALLY FLUORINATED ALCOHOLS

The present invention relates to an advantageous process for the preparation of partially fluorinated alcohols starting from halogen-containing alkenes, and 2,2,3,3,4,4-hexafluorocyclopentanol as a new partially fluorinated alcohol.

Fluorine-containing alcohols are useful intermediates for the synthesis of active compounds which can be employed in pharmacy, in agriculture or as dyestuffs (compare, for example, J. T. Welch, Tetrahedron (1987) 3123). In the agricultural sector, the partially fluorinated alcohols are suitable, in particular, as intermediates for the preparation of pest-combating agents.

Fluorine-containing alcohols additionally have good solvent properties (compare H. Liebig and K. Ulm, Chemiker Zeitung 12, 477 (1975)).

The processes known hitherto only permit the preparation of a few selected representatives from the partially fluorinated alcohols class. One process comprises the reaction of tetrafluoroethene with vinyl acetate under pressure. As a result of subsequent hydrolysis, 2,2,3,3-tetrafluorocyclobutanol is obtained in this way (W. D. Phillips, J. Chem. Phys. 25 (1956) 949). It is a disadvantage of this process that it cannot be carried out on an industrial scale, as tetrafluoroethene under pressure has a tendency to detonate explosively (H. Liebig and K. Ulm, Chemiker-Zeitung 99 (1975) 477). A further process comprises the conversion of α-hydroxycarboxylic acids into α-trifluoromethyl alcohols using sulphur tetrafluoride, which is toxic and difficult to handle. 1,1,1,4,4,4-Hexafluoro-2-butanol has been prepared in this manner (A. I. Burmakov et al., Zh. Org. Khim. 16. 1401 (1980)).

The need therefore exists for a general process, which can be simply carried out, for the preparation of partially fluorinated alcohols, which can also be used on a large scale.

An advantageous general process for the preparation of partially fluorinated alcohols of the formula (I)

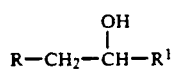
(I)

in which

R and $R^1$ are identical or different and represent alkyl which is monosubstituted or polysubstituted by fluorine, cycloalkyl which is monosubstituted or polysubstituted by fluorine or R and $R^1$ together represent the group $-(CF_2)_n-$, where n represents 2, 3 or 4, has now been found, which is characterized in that a) compounds of the formula (II)

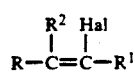
(II)

in which

R and $R^1$ have the abovementioned meaning,
$R^2$ represents hydrogen, fluorine, chlorine or bromine and Hal represents halogen,
are reacted with an alcohol of the formula (III)

(III)

in which $R^3$ represents optionally substituted radicals from the series comprising alkyl, alkenyl, cycloalkyl, cycloalkenyl, aryl, heteroaryl and aralkyl,
in the presence of a base to give compounds of the formula (IV)

(IV)

in which

R, $R^1$, $R^2$ and $R^3$ have the abovementioned meaning, and b) the compounds of the formula (IV), if desired after their isolation, are hydrogenated catalytically with hydrogen, either α) in the absence of a base to give compounds of the formula (I), or β) in the presence of a base to give compounds of the formula (V)

(V)

in which

R, $R^1$ and $R^3$ have the abovementioned meaning,
and the compounds of the formula (V) are converted, if desired after their isolation, into compounds of the formula (I) using ether-cleaving agents.

It is decidedly surprising that the process according to the invention can be carried out so simply and easily. It especially represents a general access to compounds of the formula (I) which were hitherto unavailable in industrial quantities. In particular, it is surprising that compounds of the formula (IV) can be obtained in such a good yield and purity even when $R^2$ represents halogen. It was to be expected then that the halogen atom ($R^2$) would additionally also be substituted by $OR^3$ and one or two allylic fluorine atoms would optionally be substituted (J. D. Park et al., J. Am. Chem. Soc. 73 (1951) 2342). It is furthermore surprising that the allylic fluorine atoms are not removed hydrogenolytically in the hydrogenations, as would have been expected, for example, according to the literature (compare M. Hudlicky, J. Fluorine Chem. 44, 345 (1989)). It was furthermore not to be expected that the ether cleavage would lead so selectively to the partially fluorinated alcohols of the formula (I) and no competing elimination would take place. It is particularly surprising here that the hydrogenation and the ether cleavages in step b - variant α can be carried out as "one-pot reactions", although it was to be expected that the hydrohalic acid liberated in the hydrogenation would also cleave compounds of the formula (IV).

In the formulae (I) to (V), R and $R^1$ independently of one another preferably represent alkyl having 1 to 10, preferably 1 to 8, in particular 1 to 4 carbon atoms, which is monosubstituted or polysubstituted by fluorine, cycloalkyl having 3 to 10, preferably 3 to 6, in particular 3 to 5 carbon atoms, which is monosubstituted or polysubstituted by fluorine, or R and $R^1$ together represent the group $-(CF_2)-_n$, where n represents 2, 3 or 4, n preferably represents 2 or 3 and n in particular represents 2.

For alkyl in R and $R^1$, methyl, ethyl, n- or isopropyl, n-, iso-, sec.- or tert.-butyl may be mentioned as examples. Alkyl is preferably monosubstituted to nonasubstituted by fluorine, in particular monosubstituted to pentasubstituted. Trifluoromethyl may be mentioned in particular.

For cycloalkyl in R and R¹, cyclopropyl, cyclopentyl or cyclohexyl may be mentioned as examples. The cycloalkyl radical in R and R¹, if it is substituted, is preferably monosubstituted to dodecasubstituted, in particular monosubstituted to hexasubstituted, very particularly monosubstituted to tetrasubstituted, by fluorine.

The Hal radical in the formula (II) preferably represents fluorine, chlorine or bromine, in particular fluorine or chlorine.

The R² radical in the formulae II and IV represents hydrogen, fluorine, chlorine or bromine, in particular hydrogen, fluorine or chlorine.

The R³ radical in the formulae (III) and (V) preferably represents in each case optionally substituted alkyl having 1 to 8, in particular 1 to 5 carbon atoms, alkenyl having 3 to 10, in particular 3 to 7 carbon atoms, cycloalkyl having 3 to 6 carbon atoms such as cyclopropyl, cyclopentyl or cyclohexyl, cycloalkenyl having 4 to 10, in particular 4 to 7 carbon atoms, phenyl, naphthyl, pyridyl, pyrimidyl or phenylalkyl having 1 to 4, in particular 1 or 2 carbon atoms, in the alkyl moiety. Substituents selected are halogen, in particular fluorine and chlorine, alkoxy having 1 to 10, preferably 1 to 6, in particular 1 to 4 carbon atoms, for example methoxy, ethoxy, n- or i-propoxy, and 1 or 2 oxo groups.

In particular, R³ in the formulae (III) and (V) represents primary, secondary or tertiary, preferably secondary or tertiary, alkyl having 3 to 6 carbon atoms, cyclohexyl, benzyl or phenyl. For alkyl in R³, methyl, ethyl, n-propyl, i-propyl, n-butyl, s-butyl and t-butyl may be mentioned as examples. Particularly preferred R³ represents i-propyl, phenyl, benzyl or cyclohexyl.

Partially fluorinated alkyls of the formula (I) in which R and R¹ together represent the group $-(CF_2)_n-$, where n represents 2, 3 or 4, n preferably represents 2 or 3 and n in particular represents 2, can be prepared particularly advantageously by the process according to the invention.

The course of the process according to the invention can be illustrated by the following equation:

Step a:

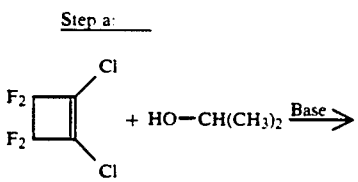

Step b (variant α):

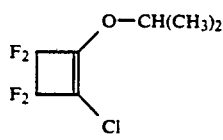

Step b (variant β):

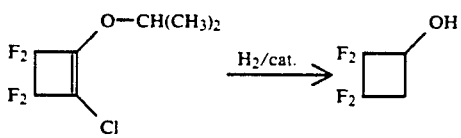

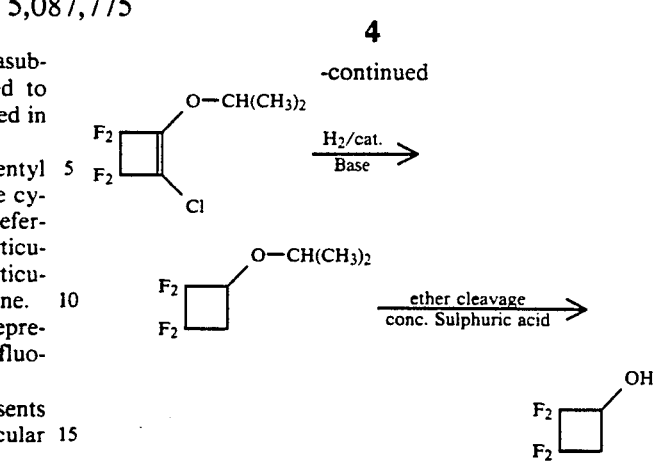

The compounds of the formulae (II) and (III) required for carrying out the process according to the invention are known synthesis chemicals or can be prepared by known methods.

The reaction of the alkene of the formula (II) with an alcohol of the formula (III) (step a) is carried out in the presence of a base and, if appropriate, in the presence of a diluent.

Suitable bases for this purposes are alkali metal and alkaline earth metal hydroxides, tertiary amines or alkoxides. Alkali metal and alkaline earth metal hydroxides and tert. amines are preferred. NaOH and triethylamine are particularly preferred.

Possible diluents for step a are all inert organic solvents. Examples of these are alkyl ethers, hydrocarbons, partially or perhalogenated hydrocarbons and also optionally substituted aromatic hydrocarbons. The alcohol of the formula (III) employed may also be used itself as a solvent. If desired, diluents can be completely dispensed with.

The reaction temperatures can be varied within a relatively wide range when carrying out the process according to the invention (step a). In general, the reaction is carried out at temperatures between −50° C. and +100° C., preferably at temperatures between −20° C. and +50° C., in particular between −20° C. and +30° C. or room temperature.

The process according to the invention is in general carried out at normal pressure, but it can also be carried out at elevated or reduced pressure.

The ratio of the materials of the formulae (II) and (III) used when carrying out the process according to the invention (step a) is not critical and may be 1:0.5 to 1:10. Ratios of 1:0.9 to 1:1.5 are preferred.

The reactions of the compounds of the formula (IV) according to step (b) are either hydrogenated, if desired after their isolation, in the absence of a base directly to give the compounds of the formula (I) (step b variant α) using hydrogen in the presence of a catalyst and if appropriate in the presence of a diluent, or reacted in the presence of a base first to give compounds of the formula (V) (hydrogenation of the double bond) and then converted using ether-cleaving agents into compounds of the formula (I) (step b - variant β).

Suitable hydrogenation catalysts are, for example, those which consist of metals and/or compounds of elements of sub-group eight of the periodic table of the elements according to Mendeleeff or contain these. The metals ruthenium, rhodium, palladium, platinum, cobalt and nickel and their compounds are preferred here. The metal compounds can be, for example, oxides, hydroxides and/or oxyhydrates. Additionally, the metals copper, vanadium, molybdenum, chromium and/or manganese, and also compounds of these metals can be present.

The hydrogenation catalysts may consist exclusively or predominantly of hydrogen-transferring substances, but the latter may also be applied to support materials. Examples of suitable support materials for the hydrogen-transferring substances are: inorganic materials such as kieselguhr, silica, aluminas, alkali metal and alkaline earth metal silicates, aluminium silicates, montmorillonite zeolites, spinels, dolomite, kaolin, magnesium silicates, zirconium oxide, zinc oxide, calcium carbonate, silicon carbide, aluminium phosphate, boron phosphate, asbestos, active carbon or barium sulphate, but also organic materials, for example naturally occurring or synthetic compounds having high molecular weights such as silk, polyamides, polystyrenes, cellulose or polyurethanes. Inorganic support materials are preferred. The support material may be present, for example, in the form of beads, extrudates, filaments, cylinders, polygons or in powder form.

Support catalysts of this type can in general contain 0.5 to 50 % by weight, preferably 1 to 10 % by weight of the hydrogen-transferring substance, relative to the total weight of the support catalyst. The hydrogen-transferring substance can in this case be homogeneously distributed in the support material, but catalysts are preferred in which the hydrogen-transferring substance is deposited in the outer layer or on the surface. The preparation and the shaping of catalysts which can be used in the process according to the invention can be carried out in a known manner (see, for example, Houben-Weyl, Methoden der organischen Chemie (Methods of Organic Chemistry), volume IV, 1c, part I, pp. 16-26, Georg Thieme Verlag, Stuttgart 1980).

Preferred support catalysts are ruthenium on carbon, ruthenium on alumina, rhodium on carbon, rhodium on alumina, palladium on carbon, palladium on alumina, palladium on calcium carbonate, palladium on barium sulphate, palladium on silica, platinum on carbon and platinum on alumina.

Preferred hydrogenation catalysts which consist exclusively or predominantly of hydrogen-transferring substance are, for example, oxide catalysts such as palladium oxide, platinum oxide, ruthenium oxide and/or rhodium oxide/platinum oxide according to Nishimura and in addition metal black catalysts, such as palladium/black, platinum/black and rhodium/black, which can be prepared by reduction of appropriate metal salts or metal salt mixtures using alkali metal hydrides, alkali metal borohydrides, metal alkyls, hydrazine, formaldehyde, hydrogen or more electropositive metals.

Particularly preferred catalysts for the process according to the invention (step b) are palladium on carbon, palladium on alumina, palladium on silica and palladium on calcium carbonate.

The hydrogenation catalyst can be employed in the process according to the invention, for example, in amounts of 0.05 to 50% by weight of hydrogen-transferring substance, relative to the total weight of the reaction mixture. This amount is preferably 0.1 to 10% by weight.

Mixtures of two or more of the hydrogenation catalysts mentioned can also be used to carry out the process according to the invention and, if appropriate, catalyst is added during the reaction.

The process according to the invention (step b) can be carried out in the liquid phase in the absence of a diluent. Preferably, however, the reaction is carried out using a diluent. Suitable diluents are all organic solvents which are inert under the reaction conditions, for example aliphatic and cycloaliphatic hydrocarbons, such as hexane, heptane, octane, cyclohexane, methylcyclohexane and decalin; aliphatic or alicyclic ethers, such as diethyl ether, dipropyl ether, diisopropyl ether, dibutyl ether, methyl butyl ether, ethyl butyl ether, ethylene glycol dimethyl ether, 1,3-dioxolane, 1,4-dioxane and tetrahydrofuran; lower aliphatic alcohols, such as methanol, ethanol, propanol, isopropanol, butanol, isobutanol, tert.-butanol and ethylene glycol; ether alcohols, such as diethylene glycol, ethylene glycol monomethyl ether, ethylene glycol monobutyl ether and dipropylene glycol. Water can also be employed. Alkanecarboxylic acids, such as acetic acid, propionic acid, hexanoic acid etc. may additionally be used.

Mixtures of two or more of the abovementioned solvents can also be used.

Preferred solvents are cycloaliphatic hydrocarbons or aliphatic ethers, in particular cyclohexane, methylcyclohexane, tetrahydrofuran, 1,4-dioxane, water and acetic acid.

If a base is used in step b, those which are suitable are, for example, alkali metal and alkaline earth metal hydroxides and carbonates, tertiary organic amines or alkoxides. Alkali metal and alkaline earth metal hydroxides and carbonates and also tertiary amines are preferred. Sodium hydroxide and potassium hydroxide, sodium carbonate and potassium carbonate, triethylamine and pyridine are particularly preferred.

The process according to the invention (step b) can be carried out in a wide temperature range. In general, the reaction according to step b is carried out at temperatures from 0° to 300° C. Preferred temperatures are from 20° to 230° C., in particular temperatures from 60° C. to 220° C.

The hydrogen pressure during the hydrogenation is not critical and may extend, for example, from 1 to 300 bar. It may be advantageous to compensate for hydrogen consumed by means of a further addition. Preferred hydrogen pressures are from 5 to 250 bar, in particular from 20 to 200 bar.

In a particular embodiment of the process according to the invention (step b - variant $\alpha$), compounds of the formula (IV) are reacted to give compounds of the formula (I) without the addition of a base, if appropriate in the presence of a diluent.

A further particular embodiment of the process according to the invention comprises the catalytic hydrogenation of compounds of the formula (IV) with the addition of a base to give compounds of the formula (V) (step b - variant $\beta$), if appropriate in the presence of a diluent. These are converted, if desired after their isolation, into compounds of the formula (I) using ether-cleaving agents.

In the hydrogenation, in the case of aromatic $R^3$ radicals, the aromatic radical can additionally be hydrogenated. In this way, the meaning of $R^3$ can be changed from, for example, phenyl to cyclohexyl (compare Preparation Example 9).

The generally known reagents, for example Bronsted and Lewis acids, can be used as ether-cleaving agents in step b, variant $\beta$. Examples of these are mineral acids such as hydrochloric acid, hydrofluoric acid, hydrobromic acid, hydriodic acid or sulphuric acid, $HBF_4$, CF₃COOH, or BF₃, FeCl₃, AlCl₃, BCl₃, BBr₃ or BI₃. So-called "soft" nucleophiles, such as, for example, iodide (for example as the lithium or potassium salt) or alkyl sulphides can also be used as ether-cleaving agents. Strong Brönsted acids and Lewis acids are preferred. HCl, sulphuric acid, FeCl₃ and BF₃ are particularly preferred.

Suitable temperatures for the ether cleavage are, for example, 0° to 300° C. If appropriate, the ether cleavage may be carried out in the presence of a diluent. It is preferred to carry out the cleavage in the absence of diluents.

The partially fluorinated alcohols of the formula (I) which can be prepared by the process according to the invention are starting materials for the synthesis of biologically active substances such as, for example, for the preparation of phosphoric acid esters which can be employed for pest-combating (compare DE-A- 38 19 632 of June 9, 1988).

Thus, for example, S-propyl O-ethyl 0-(3,3,2,2-tetrafluorocyclobutyl) thiophosphate of the formula

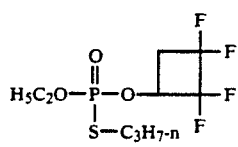

which has, inter alia, insecticidal or nematicidal action, can be prepared as follows:

289.5 g (1.5 mol) of S-propyl dichlorothiophosphate are dissolved in 4.5 l of toluene and a mixture of 69.1 g of ethanol (1.5 mol), 210 ml of triethylamine and 250 ml of toluene is added dropwise to this solution at 0° to 5° C. (about 25 min). After 5.5 hours at 0° C., 25 g of DABCO (diazabicycloundecene) and 210 ml of triethylamine are added to the reaction mixture and a mixture of 216 g (1.5 mol) of 2,2,3,3-tetrafluorocyclobutan-1-ol and 800 ml of toluene is added dropwise between 5° and 10° C. The mixture is subsequently stirred for 18 hours at 20° C., then for 3 hours at 60° C., cooled to 20° C., 3 l of water are added and the organic phase is separated off. The toluene phase is then first washed with 2 l of 1N hydrochloric acid, then with 2 l of 1N sodium hydroxide solution and finally with 3 l of water, and dried with magnesium sulphate, and the solvent is distilled off in vacuo. After distillation of the residue in a thin layer evaporator (0.1 mbar), 330 g of O-(2,2,3,3-tetrafluorocyclobutyl) O-ethyl S-propyl thiophosphate are obtained is a purity of 91% (65% of theory).

The process according to the invention is illustrated by the following examples:

EXAMPLE 1 / COMPOUND IV-1

Preparation of 2-chloro-3,3,4,4-tetrafluorocyclobutenyl isopropyl ether / step a

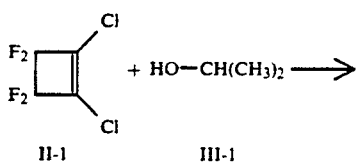

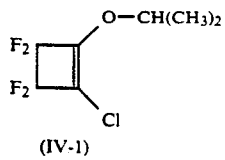

200 g (5 mol) of powdered sodium hydroxide are metered into a solution of 786 g (3.94 mol) of 1,2-dichloro-3,3,4,4-tetrafluorocyclobutene and 328 g (5.47 mol) of technical grade isopropanol at −10° C. The mixture is stirred for a further 2 hours, the solid is filtered off with suction and the filtrate is distilled.

| B.p. | 47–48° C. (24 Torr) |
|---|---|
| Yield | 747 g (85% of theory) |
| Purity | 98% |
| IR (film) | 1690 cm⁻¹ (C = C) |
| ¹H-NMR | 1.42 ppm (d, 6H), 4.87 ppm (hept., 1H) |
| ¹⁹F-NMR | −37 ppm (m, 2F), −39 ppm (m, 2F) |

EXAMPLE 2 / COMPOUND IV/2

Preparation of 2,3,3,4,4-pentafluorocyclobutenyl isopropyl ether / step a

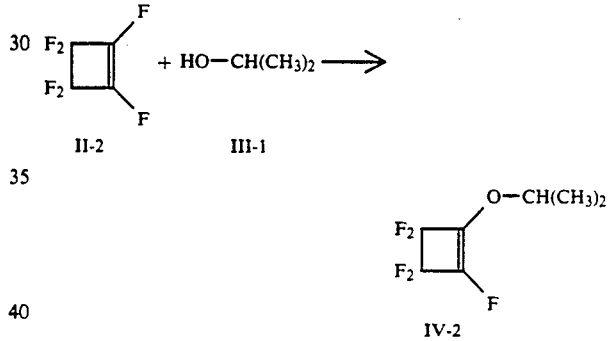

70 g (1.23 mol) of powdered potassium hydroxide are metered into a solution of 200 g (1.23 mol) of 1,2,3,3,4,4-hexafluorocyclobutene and 90 g (1:5 mol) of isopropanol in 800 ml of diethyl ether at room temperature. The mixture is stirred for a further hour and worked up as described in Example 1. The product is then distilled.

| B.p. | 64–66° C. (140 Torr) |
|---|---|
| Yield | 152 g (67% of theory) |
| Purity | 98% |
| IR | 1760 cm⁻¹ (C = C) |
| MS | 202 (M) |

EXAMPLE 3 / COMPOUND IV-3

Preparation of 2-chloro-3,3,4,4,5,5-hexafluorocyclopentenyl phenyl ether / step a

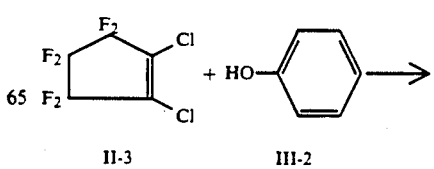

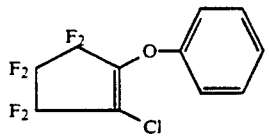

IV-3

2-Chloro-3,3,4,4,5,5-hexafluorocyclopentenyl phenyl ether is obtained from 1,2-dichloro-3,3,4,4,5,5-hexafluorocyclopentene and phenol analogously to Example 1. Yield (67% of theory; b.p. 151°–153° C.).

EXAMPLE 4 / COMPOUND IV-4

Preparation of 2-(1,1,1,4,4,4-hexafluorobut-2-enyl) benzyl ether / step a

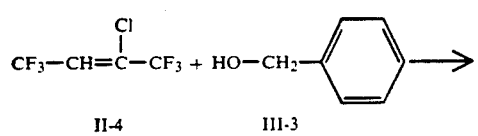

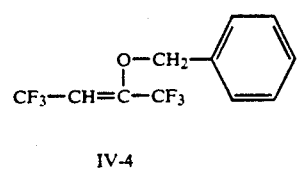

IV-4

893 g of 2-chloro-1,1,1,4,4,4-hexafluorobut-2-ene are added dropwise to a mixture of 350 g (8.75 mol) of solid sodium hydroxide and 500 g (4.63 mol) of benzyl alcohol at 20°–40° C. The mixture is stirred at 50° C. for a further two hours, poured into water and extracted with dichloromethane. The organic phases are dried and 2-(1,1,1,4,4,4-hexafluorobut-2-enyl) benzyl ether is obtained by distillation.

| Yield | 1076 g (89% of theory) |
|---|---|
| B.p. (18 mbar) | 70–72° C. |

EXAMPLE 5 / COMPOUND V-1

Preparation of 2,2,3,3-tetrafluorocyclobutyl isopropyl ether / step b (variant β)

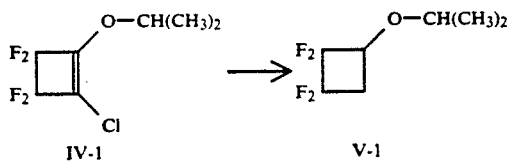

To 40 g of 10% strength palladium-carbon under nitrogen a solution of 274 g (1.26 mol) of 2-chloro-3,3,4,4-tetrafluorocyclobutenyl isopropyl ether, 252 g (2.50 mol) of triethylamine, and 1200 ml of ether dried over calcium chloride is added, and the mixture is hydrogenated in a 3 l VA autoclave at 100° C. until the pressure is constant (about 5 hours). The solid is filtered off with suction and washed well with ether, and the filtrate is washed with dilute hydrochloric acid. After drying, the organic phase is distilled.

| B.p. | 121° C. |
|---|---|
| Yield | 198 g (86% of theory) |
| Purity | 98% |
| 19F-NMR | −30 ppm (m, 2F), −39 ppm (m, 2F) |
| MS | 186 (M+), 171 (M+ − Me) |

EXAMPLE 6 / COMPOUND V-1

Preparation of 2,2,3,3-tetrafluorocyclobutyl isopropyl ether / step b (variant β)

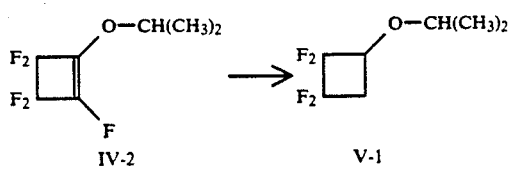

280 g (1.39 mol) of 2,3,3,4,4-pentafluorocyclobutenyl isopropyl ether are hydrogenated in 1200 ml of ether as described in Example 5 and the mixture is worked up. 2,2,3,3-Tetrafluorocyclobutyl isopropyl ether is obtained in this way in a yield of 66% of theory.

EXAMPLE 7 / COMPOUND V-1

Preparation of 2,2,3,3-tetrafluorocyclobutyl isopropyl ether / step b (variant β)

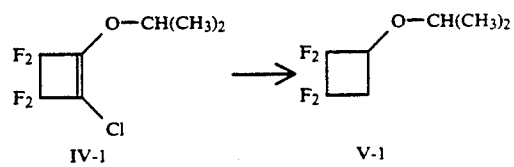

30 g (0.132 mol) of 2-chloro-3,3,4,4-tetrafluorocyclobutenyl isopropyl ether and 20 g (0.145 mol) of potassium carbonate are hydrogenated over 10 g of palladium-carbon in 100 ml of water at 120° C. for 5 hours. The catalyst is filtered off and the filtrate is extracted with dichloromethane. After drying, 2,2,3,3-tetrafluorocyclobutyl isopropyl ether is obtained with a yield of 55%.

EXAMPLE 8 / COMPOUND V-1

Preparation of 2,2,3,3-tetrafluorocyclobutyl isopropyl ether / step b (variant β)

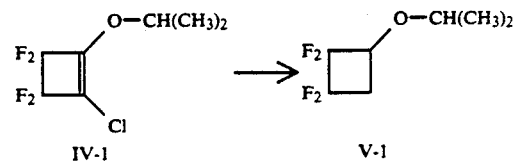

If commercially available pH 9 buffer solution (borate-hydrochloric acid) is used instead of potassium carbonate and water and the process is otherwise as described in Example 7, 2,2,3,3-tetrafluorocyclobutyl isopropyl ether is obtained with a 58 % yield.

EXAMPLE 9 / COMPOUND V-2

Preparation of 2,2,3,3,4,4-hexafluorocyclopentyl cyclohexyl ether / step b (variant β)

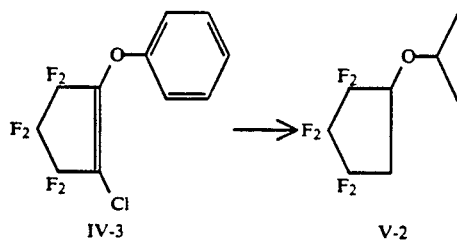

605 g (2 mol) of 2-chloro-3,3,4,4,5,5-hexafluorocyclopentenyl phenyl ether are suspended in 500 ml of pH 9 buffer (borate/HCl) in a 1.3 l autoclave and hydrogenated over 50 g of palladium-carbon at 7020 -80° C. using 80 bar of hydrogen. The mixture is worked up analogously to Example 7 and 2,2,3,3,4,4-hexafluorocyclopentyl cyclohexyl ether is obtained.

| B.p. | 86-89° C. |
|---|---|
| Yield | 502 g (91% of theory) |
| $^1$H-NMR | 1.08-1.54 ppm (m, 6H); 1.83 ppm (m, 4H); 2.34 ppm (m, 1H); 2.71 ppm (m, 1H); 3.48 ppm (m, 1H); 4.20 ppm (m, 1H) |
| $^{19}$F-NMR (against CF$_3$COOH) | −33.5 ppm (m, 2F); −47.3 ppm (m, 2F); −55.0 ppm (m, 2F) |

EXAMPLE 10 / COMPOUND V-3

Preparation of 2,2,3,3,4,4-hexafluorocyclopentyl isopropyl ether / step b (variant β)

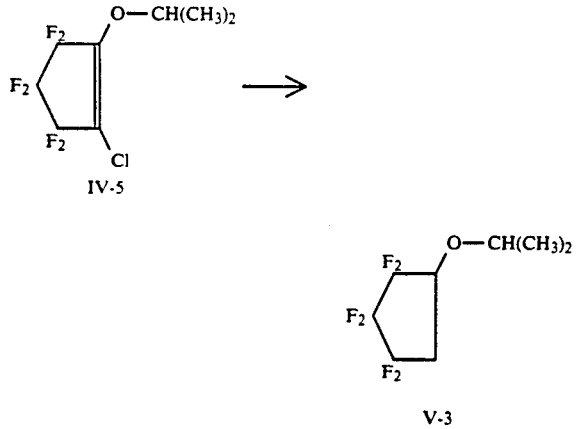

537 g (2 mol) of 2-chloro-3,3,4,4,5,5-hexafluorocyclopentyl isopropyl ether are hydrogenated analogously to Example 8 and the mixture is worked up. 2,2,3,3,4,4-Hexafluorocyclopentyl isopropyl ether is obtained.

| Yield | 419 g (89% of theory) |
|---|---|
| B.p. | 142-144° C. |
| $^1$H-NMR | 1.2 ppm (m, 6H); 2.34 ppm (m, 1H); 2.71 pppm (m, 1H); 3.82 ppm (m, 1H); 4.13 ppm (m, 1H) |

EXAMPLE 11 / COMPOUND I-1

Preparation of 1,1,1,4,4,4-hexafluorobutan-2-ol / step b (variant β) / one-pot reaction

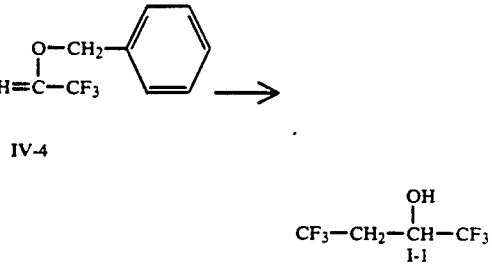

27.0 g (0.1 mol) of 2-(1,1,1,4,4,4-hexafluorobut-2-enyl) benzyl ether in 150 ml of diglyme are hydrogenated in a 300 ml autoclave over 5 g of 5% palladium-carbon using 30–40 bar of hydrogen at room temperature. The 1,1,1,4,4,4-hexafluorobutan-2-ol is obtained by distillation.

| Yield | 11.2 g (62% of theory) |
|---|---|
| B.p. | 87° C. |
| MS (CI) | 183 (M$^+$ + H) |
| IR | 3400-3100 cm$^{-1}$ (OH); 1160, 1120, 1020 cm$^{-1}$ (CF$_3$) |

EXAMPLE 12 / COMPOUND I-2

Preparation of 2,2,3,3-tetrafluorocyclobutanol / step b (variant α) / one-pot reaction

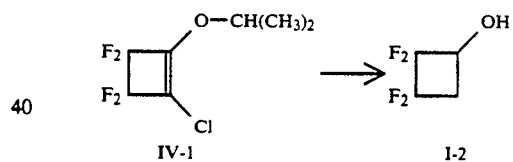

To 2.5 g of 10% strength palladium-carbon under nitrogen 50 g (0.23 mol) of 2-chloro-3,3,4,4-tetrafluorocyclobut-2-enyl isopropyl ether in 150 ml of cyclohexane are added and heated to 200° C. at a hydrogen pressure of 100 bar for 10 hours. The mixture is filtered and distilled. Pure 2,2,3,3-tetrafluorocyclobutanol is obtained.

| B.p | 121-122° C. |
|---|---|
| Purity | 99% |
| Yield | 18.6 g (56% of theory) |

EXAMPLE 13 / COMPOUND I-2

Preparation of 2,2,3,3-tetrafluorocyclobutanol / step b (variant β) - ether clevage

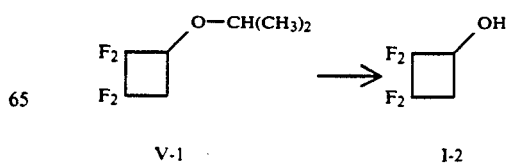

473 g (2.54 mol) of 2,2,3,3-tetrafluorocyclobutyl isopropyl ether are stirred at 140° C. with 8 g of conc. sulphuric acid until evolution of gas (propene) is complete (about 14 hours). The product is then distilled off directly.

| B.p | 120–121° C. |
|---|---|
| Yield | 345 g (96% of theory) |
| Purity | 98%/water content 1-2% (Karl Fischer) |

EXAMPLE 14 / Compound I-3

Preparation of 2,2,3,3,4,4-hexafluorocyclopentanol / step b (variant β) - ether cleavage

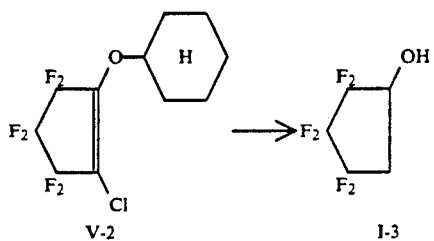

V-2    I-3

276 g (1 mol) of 2,2,3,3,4,4-hexafluorocyclopentyl cyclohexyl ether are reacted analogously to Example 13 and the mixture is worked up. 2,2,3,3,4,4-Hexafluorocyclopentanol is obtained by distillation.

| Yield | 165 g (85% of theory) |
|---|---|
| B.p. | 130–132° C. |
| $^1$H-NMR | 2.39 ppm (m, 1H); 2.72 ppm (m, 1H); 3.27 ppm (s, 1H), 4.38 ppm (m, 1H) |
| $^{19}$F-NMR (against CF$_3$COOH) | −32.2 ppm (m, 2F); −49.7 ppm (m, 2F); −54.2 ppm (m, 2F) |

It will be appreciated that the instant specification is set forth by way of illustration and not limitation, and that various modifications and changes may be made without departing from the spirit and scope of the present invention.

What is claimed is:

1. A process for the preparation of a partially fluorinated alcohol of the formula (I)

in which
R and R$^1$ are identical or different and represent C$_1$–C$_4$-alkyl which is substituted by fluorine, or R and R$^1$ together represent the group —(CF$_2$)$_n$—, wherein n represents 2, or 3, wherein a) a compound of the formula (II)

in which
R and R$^1$ have the abovementioned meaning,
R$^2$ represents hydrogen, fluorine, or chlorine and
Hal represents halogen,
are reacted with an alcohol of the formula (III)

HO—R$^3$    (III)

in which
R$^3$ represents C$_1$–C$_5$-alkyl, C$_3$–C$_6$-cycloalkyl, benzyl or phenyl,
in the presence of a base to give a compound of the formula

in which
R, R$^1$, R$^2$ and R$^3$ have the abovementioned meaning, and (b) the compound of the formula (IV), after its isolation, is hydrogenated catalytically with hydrogen in the presence of a base to give a compound of the formula (V)

in which
R, R$^1$ and R$^3$ have the abovementioned meaning, and the compound of the formula (V) is converted, after its isolation, into a compound of the formula (I) using an ether-cleaving agent selected from the group consisting of HCl, sulphuric acid, FeCl$_3$ and BF$_3$.

2. A process according to claim 1, wherein an alkali metal or alkaline earth metal hydroxide, tertiary amine or alkoxide is employed as the base in step a.

3. A process according to claim 1, wherein step a is carried out in the presence of a diluent or an excess of an alcohol of the formula (III).

4. A process according to claim 1, wherein step b is carried out in the presence of a diluent.

5. A process according to claim 1, wherein an alkali metal and alkaline earth metal hydroxide, alkaline earth metal carbonate, tertiary organic amine or alkoxide is used in step b.

6. A process according to claim 1, wherein the step b is carried out an a one-pot reaction.

7. A process for the preparation of a compound of the formula (IV)

in which
R and R$^1$ are identical or different and represent C$_1$–C$_4$ alkyl which is substituted by fluorine, or R and R$^1$ together represent the group —(CF$_2$)$_n$—, where n represents 2 or 3, R$^2$ represents hydrogen, fluoride or chlorine and R$^3$ represents C$_1$–C$_5$ alkyl, C$_3$–C$_6$ cycloalkyl, benzyl or phenyl wherein a compound of the formula (II)

in which

R, R¹, R² have the abovementioned meaning and Hal represents halogen, are reacted with an alcohol of the formula (III)

$$HO-R^3 \qquad (III)$$

in which

R³ has the abovementioned meaning, in the presence of a base.

8. A process for the preparation of a compound of the formula (I)

$$R-CH_2-\underset{\underset{OH}{|}}{CH}-R^1 \qquad (I)$$

in which

R and R¹ have the abovementioned meaning R² represents hydrogen, fluorine, or chlorine and R³ represents C₁-C₅ alkyl, C₁-C₆ cycloalkyl, benzyl or phenyl and a wherein a compound of the formula $$R-\underset{\underset{R^2}{|}}{C}=\underset{\underset{R^1}{|}}{C}-R^1 \quad\substack{O-R^3\\|} \qquad (VI)$$

in which

R, and R¹ are identical or different and represent C₁-C₄ alkyl which is substituted by fluorine, or R and R¹ represent the group —(CF₂)ₙ—, where n represents 2, is hydrogenated catalytically with hydrogen in the presence of a base to give a compound of the formula (V)

$$R-CH_2-\underset{\underset{O-R^3}{|}}{CH}-R^1 \qquad (V)$$

in which

R, R¹ and R³ have the abovementioned meaning, and a compound of the formula (V) is converted, after its isolation, into a compound of the formula (I) using an ether-cleaving agent.

* * * * *

UNITED STATES PATENT AND TRADEMARK OFFICE
CERTIFICATE OF CORRECTION

PATENT NO. : 5,087,775
DATED : February 11, 1992
INVENTOR(S) : Gassen, et al

It is certified that error appears in the above-indentified patent and that said Letters Patent is hereby corrected as shown below:

Col. 13, line 57    Delete 1st " wherein " and substitute -- where --

Col. 14, line 11    Delete " (VI) " and substitute -- (IV) --

Col. 16, line 3     Delete " (VI) " and substitute -- (IV) --

Signed and Sealed this

Eighth Day of February, 1994

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,087,775
DATED : February 11, 1992
INVENTOR(S) : Gassen et al

It is certified that error appears in the above-indentified patent and that said Letters Patent is hereby corrected as shown below:

Col. 15, line 22, delete "$C_1-C_6$ cycloalkyl" and substitute --$C_3-C_6$-cycloalkyl--.

Signed and Sealed this

Thirtieth Day of August, 1994

Attest:

Attesting Officer

BRUCE LEHMAN

Commissioner of Patents and Trademarks